United States Patent
Yabusaki

(10) Patent No.: US 8,790,885 B2
(45) Date of Patent: Jul. 29, 2014

(54) COAGULOGEN RAW MATERIAL, PROCESS FOR PRODUCING THE SAME, AND METHOD AND APPARATUS FOR MEASURING PHYSIOLOGICALLY ACTIVE SUBSTANCE OF BIOLOGICAL ORIGIN USING THE SAME

(75) Inventor: Katsumi Yabusaki, Hamamatsu (JP)

(73) Assignee: Kowa Company, Ltd., Aichi (JP)

( * ) Notice: Subject to any disclaimer, the term of this patent is extended or adjusted under 35 U.S.C. 154(b) by 369 days.

(21) Appl. No.: 13/202,285

(22) PCT Filed: Feb. 19, 2010

(86) PCT No.: PCT/JP2010/052551
§ 371 (c)(1),
(2), (4) Date: Oct. 4, 2011

(87) PCT Pub. No.: WO2010/095718
PCT Pub. Date: Aug. 26, 2010

(65) Prior Publication Data
US 2012/0040385 A1    Feb. 16, 2012

(30) Foreign Application Priority Data

Feb. 19, 2009  (JP) .................................. 2009-037150

(51) Int. Cl.
| | | |
|---|---|---|
| *G01N 33/579* | (2006.01) | |
| *C12Q 1/56* | (2006.01) | |
| *G01N 21/82* | (2006.01) | |
| *C12Q 1/37* | (2006.01) | |
| *C12Q 1/04* | (2006.01) | |
| *G01N 33/86* | (2006.01) | |

(52) U.S. Cl.
CPC .............. *G01N 33/579* (2013.01); *G01N 21/82* (2013.01); *C12Q 1/37* (2013.01); *C12Q 1/04* (2013.01); *G01N 33/86* (2013.01)
USPC .................. 435/13; 435/7.1; 435/7.2; 436/69; 436/71

(58) Field of Classification Search
None
See application file for complete search history.

(56) References Cited

U.S. PATENT DOCUMENTS

| | | | |
|---|---|---|---|
| 4,322,217 | A | 3/1982 | Dikeman |
| 5,316,911 | A | 5/1994 | Baek et al. |
| 5,389,547 | A | 2/1995 | Tanaka et al. |
| 5,476,772 | A | 12/1995 | Tsuchiya et al. |
| 6,156,519 | A | 12/2000 | Tamura et al. |

| | | | |
|---|---|---|---|
| 2006/0216780 | A1 | 9/2006 | Wainwright et al. |
| 2010/0129260 | A1 | 5/2010 | Shirasawa |
| 2013/0183763 | A1 | 7/2013 | Obata et al. |

FOREIGN PATENT DOCUMENTS

| | | |
|---|---|---|
| CN | 1087724 A | 6/1994 |
| CN | 1469124 A | 1/2004 |
| CN | 1621841 A | 6/2005 |
| CN | 1632579 A | 6/2005 |
| CN | 101368967 A | 2/2009 |
| EP | 0613004 A1 | 8/1994 |
| JP | 4-76459 A | 3/1992 |
| JP | 06-118086 | 4/1994 |
| JP | 2667695 | 10/1997 |
| JP | 10-293129 | 11/1998 |
| JP | 2004-061314 | 2/2004 |
| JP | 2008-526257 | 7/2008 |
| JP | 2009-085880 | 4/2009 |
| WO | WO 2008/010902 | 1/2008 |
| WO | WO 2008/038329 A1 | 4/2008 |
| WO | WO 2008/139544 A1 | 11/2008 |

OTHER PUBLICATIONS

Office Action issued in Chinese Patent Application No. 201080008580.9 on Jun. 3, 2013.
Nakamura et al., "A Clottable Protein (Coagulogen) from Amoebocyte Lysate of Japanese Horseshoe Crab (*Tachypleus tridentatus*) Its Isolation and Biochemical Properties," *The Journal of Biochemistry*, vol. 80(5), pp. 1011-1021 (1976).
Wang et al., "Fast Purification of Coagulogen from Commercial Limulus Reagents," *Academic Journal of Kunming Medical College*, vol. 16(2), pp. 18-21 (Jun. 1995).
Yabusaki, et al. "Simplified Preparation of Crude and functional Coagulogen by Thermal Inactivation of Serine Proteases in *Limulus* Amebocyte Lysate and its Application for Rapid Endotoxin Determination," *Journal of Bioscience and Bioengineering*, vol. 113, No. 3, pp. 406-411, 2012.
Extended European Search Report dated Jun. 6, 2012 and issued to corresponding European application No. 10743843.4.
International Search Report issued Mar. 16, 2010, issued to international application No. PCT/JP2010/052551.

*Primary Examiner* — Marsha Tsay
(74) *Attorney, Agent, or Firm* — Knobbe, Martens, Olson & Bear LLP

(57) ABSTRACT

Disclosed is a technique for obtaining a coagulogen raw material which can irreversibly inactivate the activity of a coagulase while retaining the function of coagulogen in an LAL reagent, a LAL reagent contaminated by an organism-derived biologically active substance or the like, and which can be used in a reagent. An LAL reagent is heated at a predetermined temperature for a predetermined period of time to deactivate only the activity of an enzyme contained in the LAL reagent irreversibly, wherein such an activity inherent in coagulogen that coagulogen can be hydrolyzed with the activated coagulase and converted to coagulin to induce gelatinization or an agglutination reaction is retained.

2 Claims, 6 Drawing Sheets

COAGULOGEN RAW MATERIAL, PROCESS FOR PRODUCING THE SAME, AND METHOD AND APPARATUS FOR MEASURING PHYSIOLOGICALLY ACTIVE SUBSTANCE OF BIOLOGICAL ORIGIN USING THE SAME

CROSS-REFERENCE TO RELATED APPLICATIONS

This application is the U.S. National Phase under 35 U.S.C. §371 of International Application PCT/JP2010/052551, filed Feb. 19, 2010, which was published in a non-English language, which claims priority to JP Application No. 2009-037150, filed Feb. 19, 2009.

TECHNICAL FIELD

The present invention relates to a reagent for carrying out detection or concentration measurement of physiologically active substance of biological origins such as endotoxin and β-D-glucan rapidly or with a high sensitivity, a process for producing the same, and a measuring method and a measuring apparatus using the same.

BACKGROUND ART

Endotoxin is a lipopolysaccharide present in a cell wall of a Gram-negative bacterium and is the most typical pyrogen. If a transfusion, a medicine for injection, blood or the like contaminated with the endotoxin enters into a human body, the endotoxin may induce severe side effects such as fever and shock. Therefore, it is required to manage the above-mentioned medicines so that they are not contaminated with endotoxin.

By the way, a hemocyte extract of limulus (hereinafter, also referred to as "limulus amoebocyte lysate (LAL)") contains serine protease that is an enzyme activated by endotoxin. When LAL reacts with endotoxin, a coagulogen present in LAL is hydrolyzed into a coagulin by an enzyme cascade by the serine protease activated according to the amount of endotoxin, and the coagulin is associated to form an insoluble gel. With the use of this property of LAL, it is possible to detect endotoxin with a high sensitivity.

Furthermore, β-D-glucan is a polysaccharide that constitutes a cell membrane characteristic of a fungus. Measurement of β-D-glucan is effective, for example, for screening of infectious diseases due to a variety of fungi including not only fungi that are frequently observed in general clinical practices, such as *Candida, Aspergillus*, and *Cryptococcus*, but also rare fungi.

Also in the measurement of β-D-glucan, by using the property of the limulus amoebocyte lysate to coagulate (coagulate to form a gel) by β-D-glucan, the β-D-glucan can be detected with a high sensitivity.

A method for detection or concentration measurement of a physiologically active substance of biological origin (hereinafter, also referred to as a "predetermined physiologically active substance") such as endotoxin and β-D-glucan, which can be detected by a limulus amoebocyte lysate, includes a semi-quantitative gelation method which includes: by allowing a liquid mixture obtained by mixing a sample to be subjected to detection or concentration measurement of the predetermined physiologically active substance (hereinafter, also simply referred to as "measurement of the predetermined physiologically active substance") with a reagent produced based on LAL (LAL reagent) to stand still; inverting the container after a lapse of a predetermined time; and determining whether or not the sample is gelled based on the presence or absence of dipping of the sample so as to examine whether or not the sample contains endotoxin of a certain concentration or more. Examples of the method include a turbidimetric method including analyzing a sample by measuring over time the turbidity of the sample caused by gel formation by a reaction between LAL reagent and the predetermined physiologically active substance, a colorimetric method using a synthetic substrate that is hydrolyzed by an enzyme cascade to develop a color, and other methods.

In the case where a predetermined physiologically active substance is measured by the above-mentioned turbidimetric method, a liquid mixture of a measurement sample and an LAL reagent is produced in a dry-heat-sterilized glass measurement cell. Then, gelation of the liquid mixture is optically measured from the outside. However, the turbidimetric method may require a very long time for gelation of the liquid mixture particularly in a sample with a low concentration of the predetermined physiologically active substance. To solve the problem, a method that can measure the predetermined physiologically active substance in a short time has been required. There has been proposed a laser light scattering particle counting method capable of forming gel fine particles by stirring a liquid mixture of a measurement sample and an LAL reagent using, for example, a magnetic stirring bar, and measuring the presence of the predetermined physiologically active substance in the sample in a short time based on the intensity of laser light scattered by the gel particles or based on the intensity of light transmitted through the liquid mixture.

The LAL reagent is produced by using limulus amoebocyte lysate as a principal raw material. Therefore, in production, endotoxin or β-D-glucan may enter with a certain probability, and the resultant product may be a waste that cannot be used as a reagent. Furthermore, since the measurement methods of any of endotoxin and β-D-glucan use a limulus amoebocyte lysate that is a limited resource as a raw material of the measurement reagent, it is necessary to reduce the amount of use of the reagent, or to reduce the production loss in producing the reagent.

As an attempt to reduce the amount of use of the reagent, not only simply reducing the volume of samples, but also enhancing the measurement sensitivity to consequently reduce the number of measurement times is effective. Meanwhile, for reducing the loss in production, it is important to suppress contamination with endotoxin or β-D-glucan. In addition, it should also be considered to remove endotoxin or β-D-glucan from a raw material that becomes unusable as a reagent during production and to reuse it as an auxiliary additive of the reagent. When the raw material is used as an auxiliary additive of the reagent, the use to be thought includes use as a coagulogen raw material that plays a role as an agent of adjusting the viscosity of a reagent, or a central role in gelation and aggregation.

However, it is impossible to remove an enzyme group, which has already been activated, only by removing endotoxin in the raw material that is contaminated with, for example, endotoxin and that cannot be used. A method for manufacturing a raw material, in which only an enzymatic activity in the raw material is inactivated while maintaining the function of coagulogen, that is, the function of being hydrolyzed by an activated clotting enzyme and converted into a coagulin to cause gelation and an aggregation reaction, has not been reported.

CITATION LIST

Patent Literature

Patent Document 1: Japanese Patent No. 2667695
Patent Document 2: Japanese Patent Application Laid-Open No. 2004-061314
Patent Document 3: Japanese Patent Application Laid-Open No. 10-293129

SUMMARY OF INVENTION

Technical Problem

The present invention has been made in view of the above-mentioned problems. An object of the present invention is to provide a technique for obtaining a coagulogen raw material which can be used as a reagent, which can irreversibly inactivate the activity of clotting enzyme while maintaining the function of coagulogen in an LAL reagent, an LAL reagent contaminated with a physiologically active substance of biological origin, or the like.

Solution to Problem

In order to solve the above-mentioned problems, the greatest characteristic of the present invention is that an LAL reagent in which some predetermined physiologically active substances are allowed to enter is heat-treated under certain temperature conditions to irreversibly deactivate only an enzymatic activity in the LAL reagent. In the present invention, at this time, such an activity inherent in coagulogen that coagulogen can be hydrolyzed with an activated clotting enzyme and converted into a coagulin to induce gelation and an aggregation reaction is maintained.

More specifically, the present invention is a process for producing a coagulogen raw material used for detecting a predetermined physiologically active substance of biological origin or measuring a concentration of the physiologically active substance, wherein an LAL that is limulus amoebocyte lysate containing a predetermined enzyme group and a coagulogen is allowed to react with the physiologically active substance, and a phenomenon that the coagulogen is hydrolyzed into a coagulin by an enzyme cascade generated when the enzyme group is activated by the physiologically active substance is used, and the LAL is heat-treated at a predetermined temperature for a predetermined period of time to deactivate at least a part of the enzyme group in the LAL while maintaining an activity of the coagulogen.

According to this, by deactivating at least a part of the enzyme group constituting the enzyme cascade in the LAL so as to inhibit the generation of the enzyme cascade, thus making it possible to obtain a coagulogen raw material that is hard to be hydrolyzed into a coagulin due to contamination with endotoxin, β-D-glucan, or the like.

Furthermore, according to this, coagulogen in the LAL reagent, which cannot be used due to contamination with endotoxin, β-D-glucan, or the like, can be obtained while the function is maintained, and therefore, this makes it possible to more effectively use limited resource obtained from the limulus blood cells.

Herein, the predetermined enzyme group signifies enzymes such as factor C, factor B, factor G, precursor of clotting enzyme, in LAL, which cause generation of an enzyme cascade by endotoxin, β-D-glucan, or the like, and generation of clotting enzyme finally hydrolyzing coagulogen. That is, an object of the present invention can be achieved when clotting enzyme finally hydrolyzing coagulogen is not generated due to endotoxin, β-D-glucan, or the like, by deactivating at least a part of enzyme without deactivating all enzymes in LAL.

Furthermore, in the above description, the predetermined physiologically active substance of biological origin denotes a physiologically active substance having characteristics of activating a predetermined enzyme group in LAL to generate an enzyme cascade, and generating clotting enzyme that finally hydrolyzes coagulogen. Examples of such substances include endotoxin and β-D-glucan as mentioned above. However, it is intended that the substances include other physiologically active substances having the equivalent properties, and the substances are not limited to the above-mentioned two substances.

Note that in the above description, when the LAL is supplied as a solution, the predetermined temperature may be 60° C. or more. Herein, the present inventors have made intensive studies and found that by heat-treating the LAL reagent as a solution to 60° C. or more, the enzymatic activity of the enzyme group such as serine protease can be deactivated substantially completely. Therefore, by setting the predetermined temperature to 60° C. or more, when the LAL is supplied as a solution, it is possible to more reliably obtain a coagulogen raw material that is not hydrolyzed into a coagulin even if it is contaminated with endotoxin, β-D-glucan, or the like.

Furthermore, in the above description, when the LAL is supplied as a solution, the predetermined temperature may be 80° C. or less. Herein, the inventors of the present invention have made intensive studies and found that by heat-treating the LAL reagent to a temperature of higher than 80° C. so as to deactivate the enzymatic activity, the reagent becomes turbid due to denaturation of protein in LAL. In this case, the LAL reagent may not be suitable for an object for carrying out detection or concentration measurement of the predetermined physiologically active substance by optical technique by transmitted light or the scattered light with respect to the reagent. Therefore, in the present invention, when the LAL is supplied as a solution, by setting the predetermined temperature at 80° C. or less, a coagulogen raw material of high utility value, which is suitable for optical measurement, can be obtained.

In addition, in the above description, when the LAL is supplied as a solution, the predetermined period of time may be 10 minutes or more and 8 hours or less. Herein, it has been revealed that when the LAL reagent as a solution is heat-treated to 60° C. or more, with the heating time of about 10 minutes, the enzymatic activity of the enzyme group such as serine protease can be deactivated substantially completely. Therefore, by setting the predetermined period of time at 10 minutes or more, the enzymatic activity of the enzyme group such as serine protease can be deactivated substantially completely in a wide range of heating temperatures. Furthermore, when the heating time is extremely long, protein in LAL may be denatured and become turbid even at low temperatures. Therefore, in the present invention, by setting the predetermined period of time at 10 minutes or more and 8 hours or less, it is possible to more reliably obtain a coagulogen raw material that is suitable for optical measurement and that is not hydrolyzed into a coagulin even if it is contaminated with endotoxin, β-D-glucan, or the like.

In addition, in the above description, when the LAL is supplied as a freeze-dried product, the predetermined temperature may be 100° C. or more and 250° C. or less. Herein, it has been revealed that when the LAL is supplied as a freeze-dried product, heat treatment needs to be carried out at higher temperatures as compared with the case where the LAL is supplied as a solution. In this case, when the LAL reagent is heat-treated at 100° C. or more and 250° C. or less, it is possible to more reliably obtain a coagulogen raw material of higher utility value, which is not hydrolyzed into a coagulin even if it is contaminated with endotoxin, β-D-glucan, or the like, and which is suitable for optical measurement.

Also, in this case, the predetermined period of time may be 300 minutes or more. Herein, it has been revealed that when the LAL is supplied as a freeze-dried product, by heating the LAL reagent at 120° C. for 300 minutes, the enzymatic activity of the enzyme group such as serine protease can be deactivated substantially completely. Therefore, by setting the predetermined period of time at 300 minutes or more, it is possible to more reliably obtain a coagulogen raw material that is not hydrolyzed into a coagulin even if it is contaminated with endotoxin, β-D-glucan, or the like, in the wider range of heating temperatures.

The present invention may also be a coagulogen raw material used for detecting a predetermined physiologically active substance of biological origin or measuring a concentration of the physiologically active substance, wherein a LAL that is limulus amoebocyte lysate containing a predetermined enzyme group and coagulogen is allowed to react with the physiologically active substance, and a phenomenon that coagulogen is hydrolyzed into a coagulin by an enzyme cascade generated when the enzyme group is activated by the physiologically active substance is used, and the LAL is heat-treated at a predetermined temperature for a predetermined period of time to deactivate at least a part of the enzyme group in the LAL.

In this coagulogen raw material, since the enzyme group that generates an enzyme cascade is deactivated by the reaction with a predetermined physiologically active substance, it is possible to inhibit coagulogen from being hydrolyzed into a coagulin by contamination with a small amount of predetermined physiologically active substance, and thus a coagulogen raw material that can be easily handled can be obtained. Note that also in this case, when the LAL is supplied as a solution, the predetermined temperature may be 60° C. or more. Also, the predetermined temperature may be 80° C. or less. Furthermore, the predetermined period of time may be 10 minutes or more and 8 hours or less. On the other hand, when the LAL is supplied as a freeze-dried product, the predetermined temperature may be 100° C. or more and 250° C. or less. Also, the predetermined period of time may be 300 minutes or more.

The present invention may also be an LAL reagent that is used for detecting a physiologically active substance or measuring a concentration of the physiologically active substance, wherein the coagulogen raw material obtained above and LAL that has not been heat-treated are blended with each other so as to increase a concentration of the coagulogen in the LAL that has not been heat-treated.

That is, when a coagulin raw material in which a predetermined enzyme group is deactivated is added to LAL that has not been heat-treated, it is possible to prepare an LAL reagent having a coagulogen concentration that is higher than usual. This can relatively increase the amount of coagulogen that can be hydrolyzed into a coagulin with an enzyme group that has been activated by a reaction with a predetermined physiologically active substance. Therefore, gelation of the LAL reagent by a predetermined physiologically active substance can be made remarkable, thus enabling the measurement of the predetermined physiologically active substance more sensitive.

The present invention may also be coagulogen-bound microbeads for measuring endotoxin, which are prepared by allowing coagulogens in the coagulogen raw material obtained above to be bound or adsorbed to surfaces of a large number of fine particles having a larger diameter than the coagulogen.

Herein, it has been revealed that when a predetermined physiologically active substance such as endotoxin is allowed to act on LAL in a state in which coagulogen is bound or adsorbed to, for example, resin fine particles, a larger aggregated cluster is generated earlier as compared with the case in which the predetermined physiologically active substance is acted on a LAL simple substance. This is because the coagulogen on fine particles is hydrolyzed into a coagulin by an enzyme cascade in the LAL, which allows fine particles to be associated with each other. Furthermore, it has been clear that this aggregation reaction is less likely to be affected by a turbidity or color of the sample, and furthermore, this aggregation reaction is extremely stronger than the aggregation reaction induced by a LAL simple substance.

The present invention uses these phenomena, and prepares a reagent (hereinafter, also referred to as "coagulogen-bound microbeads") in which a coagulogen raw material obtained by deactivating an enzyme group in LAL is allowed to be bound or adsorbed to fine particles. When a sample containing endotoxin is allowed to act on a reagent obtained by blending the coagulogen-bound microbeads with LAL, the coagulogen originally present in LAL is converted into a coagulin and the coagulin is aggregated. At the same time, the coagulogen bound or adsorbed to fine particles is converted into a coagulin to associate the fine particles with each other and a larger aggregated cluster can be formed in the early stage. This can significantly promote formation of gel particles in the liquid mixture of an LAL reagent and a sample. As a result, it is possible to carry out detection or concentration measurement of predetermined physiologically active substances more rapidly and with a high sensitivity.

To bind or adsorb the coagulogen contained in LAL to the fine particles, first, a functional group capable of binding or adsorbing the proteins is allowed to be present on the surfaces of the fine particles. Then, according to conventional methods, in such a state, the LAL is allowed to act on the functional group to chemically bind or electrostatically, hydrophilically, or hydrophobically adsorb the coagulogen to the surfaces of the fine particles. In this case, it takes a long period of time to carry out the reaction in LAL. Therefore, it is thought that in conventional methods, a minute amount of predetermined physiologically active substances which are present together in fine particles, reagents to be used, or water may react with the enzyme group in the proteins to hydrolyze the coagulogen into the coagulin, which may start aggregation of the fine particles during binding and adsorbing reaction between coagulogen and fine particles. In this case, the coagulogen in the reagent may be hydrolyzed and consumed by activation of the enzyme.

In order to solve such a problem, conventionally, when coagulogen is allowed to be bound or adsorbed to the surface of fine particles, it is necessary that an LAL reagent and a suspension of fine particles be blended with each other, and that an inhibitor for inhibiting the reaction between the enzyme group in the LAL and the predetermined physiologically active substance be added. Consequently, an operation for allowing the coagulogen to be bound or adsorbed on the surface of the fine particles is complicated and disadvantageous in cost. On the contrary, in the present invention, since the enzyme group in LAL is deactivated during the preparation of the coagulogen raw material, a step of adding an inhibitor can be omitted. Thus, it is possible to prepare a reagent in which coagulogen is allowed to be bound or adsorbed to fine particles in a simpler way or at a lower cost.

Furthermore, the present invention may be a method for measuring a physiologically active substance of biological origin, the method including detecting the predetermined physiologically active substance or measuring a concentration of the predetermined physiologically active substance, wherein the LAL reagent whose coagulogen concentration in LAL that has not been heat-treated is increased is mixed with a reagent containing the predetermined physiologically active substance by mixing the above-mentioned coagulogen material with the LAL that has not been heat-treated with each other, and a phenomenon that the coagulogen whose concentration is increased is hydrolyzed into a coagulin by an enzyme cascade generated when the enzyme group in the LAL reagent is activated by the predetermined physiologically active substance is used.

According to the method for measuring a physiologically active substance of biological origin, it is possible to measure a predetermined physiologically active substance by using coagulogen having a higher concentration. Therefore, gelation by the reaction between a predetermined physiologically active substance and a LAL can be made remarkable, and the measurement of the predetermined physiologically active substance can be carried out with higher sensitivity.

Furthermore, the present invention may be a method for measuring a physiologically active substance of biological origin, the method including: detecting the predetermined physiologically active substance or measuring a concentration of the predetermined physiologically active substance, wherein the above-mentioned coagulogen-bound microbeads, a LAL that has not been heat-treated, and a sample containing the predetermined physiologically active substance are mixed with each other, and a phenomenon that coagulogen that is bound or adsorbed to the surface of the fine particles by an enzyme cascade generated when the enzyme group in the LAL that has not been heat-treated is activated by the predetermined physiologically active substance is hydrolyzed into a coagulin and that the fine particles are cross-linked to each other is used.

According to the method for measuring the predetermined physiologically active substance, a sample containing endotoxin is allowed to act on a reagent obtained by blending coagulogen-bound microbeads on which a coagulogen raw material obtained by deactivating the enzyme group in the LAL is bound or adsorbed to fine particles and LAL that has not been heat-treated. Thus, coagulogen originally existing in the LAL is made into a coagulin and aggregated, and the coagulogen bound or adsorbed onto fine particles is made into a coagulin so as to associate fine particles with each other to generate a larger aggregated cluster in the early stage. Thus, it is possible to significantly promote generation of gel particles in a liquid mixture of the LAL reagent and the sample. As a result, it is possible to carry out detection or concentration measurement of physiologically active substance of biological origins more rapidly and with a high sensitivity.

Furthermore, the present invention may be a stirring turbidimetric measurement apparatus for a physiologically active substance of biological origin, which includes a liquid mixture retaining portion for retaining a liquid mixture such that light can be incident, and allowing a reaction in the liquid mixture to proceed, the liquid mixture including the coagulogen-bound microbeads mentioned above, an LAL that has not been heat-treated, and a sample including the predetermined physiologically active substance;

a stirring portion for stirring the liquid mixture in the liquid mixture retaining portion;

a light incidence portion for allowing light to be incident into the liquid mixture in the liquid mixture retaining portion;

a light receiving portion for receiving transmitted light in the liquid mixture in the incident light and converting it into an electric signal; and a deriving portion for deriving a concentration of the physiologically active substance in the sample from transmittance of the liquid mixture obtained from the electric signal converted in the light receiving portion.

In the present invention, coagulogen-bound microbeads in which a coagulogen raw material obtained by deactivating the enzyme group in the LAL is bound or adsorbed onto fine particles, LAL that has not been heat-treated, and a sample containing a predetermined physiologically active substance are mixed with each other. The mixture is placed in the liquid mixture retaining portion. Then, the liquid mixture is stirred by the stirring portion, thereby promoting hydrolysis of coagulogen with clotting enzyme activated by a predetermined physiologically active substance and association of fine particles by a coagulin obtained by hydrolysis.

Then, among light incident from the light incidence portion, the intensity of the light that has transmitted the liquid mixture and reached a light receiving element is measured. Furthermore, in the deriving portion, from the transmittance of the above-mentioned liquid mixture, the concentration of a predetermined physiologically active substance is derived.

Herein, when the hydrolysis of coagulogen bound or adsorbed onto fine particles proceeds and a coagulin is generated, the coagulin associates fine particles to each other so as to generate a larger aggregated cluster in the early stage. Herein, the liquid mixture of coagulogen-bound microbeads, LAL that has not been heat-treated and a sample containing a predetermined physiologically active substance is highly turbid at the time when they are mixed because a large number of fine particles of microbeads are dispersed. Then, when the association of fine particles generated by a coagulin proceeds, since the concentration of fine particles is rapidly reduced, the transmittance of the liquid mixture is rapidly increased.

In the stirring turbidimetric measurement apparatus according to the present invention, unlike a measurement device according to a usual turbidimetric method, the rapid increase in transmittance caused by the association of fine particles accompanying the generation of a coagulin is measured. Thus, together with the effect of promoting the reaction by stirring the liquid mixture, it is possible to significantly shorten the measurement time, and carry out measurement of a predetermined physiologically active substance with extremely high sensitivity.

Note that the above-mentioned solutions to the problem of the present invention can be used in combination as much as possible.

Advantageous Effects of Invention

In the present invention, a coagulogen raw material which can be used as a reagent and which can irreversibly inactivate the activity of clotting enzyme while maintaining the function of coagulogen in an LAL reagent, or an LAL reagent contaminated with a physiologically active substance of biological origin or the like can be obtained.

DESCRIPTION OF EMBODIMENTS

Figure 6:
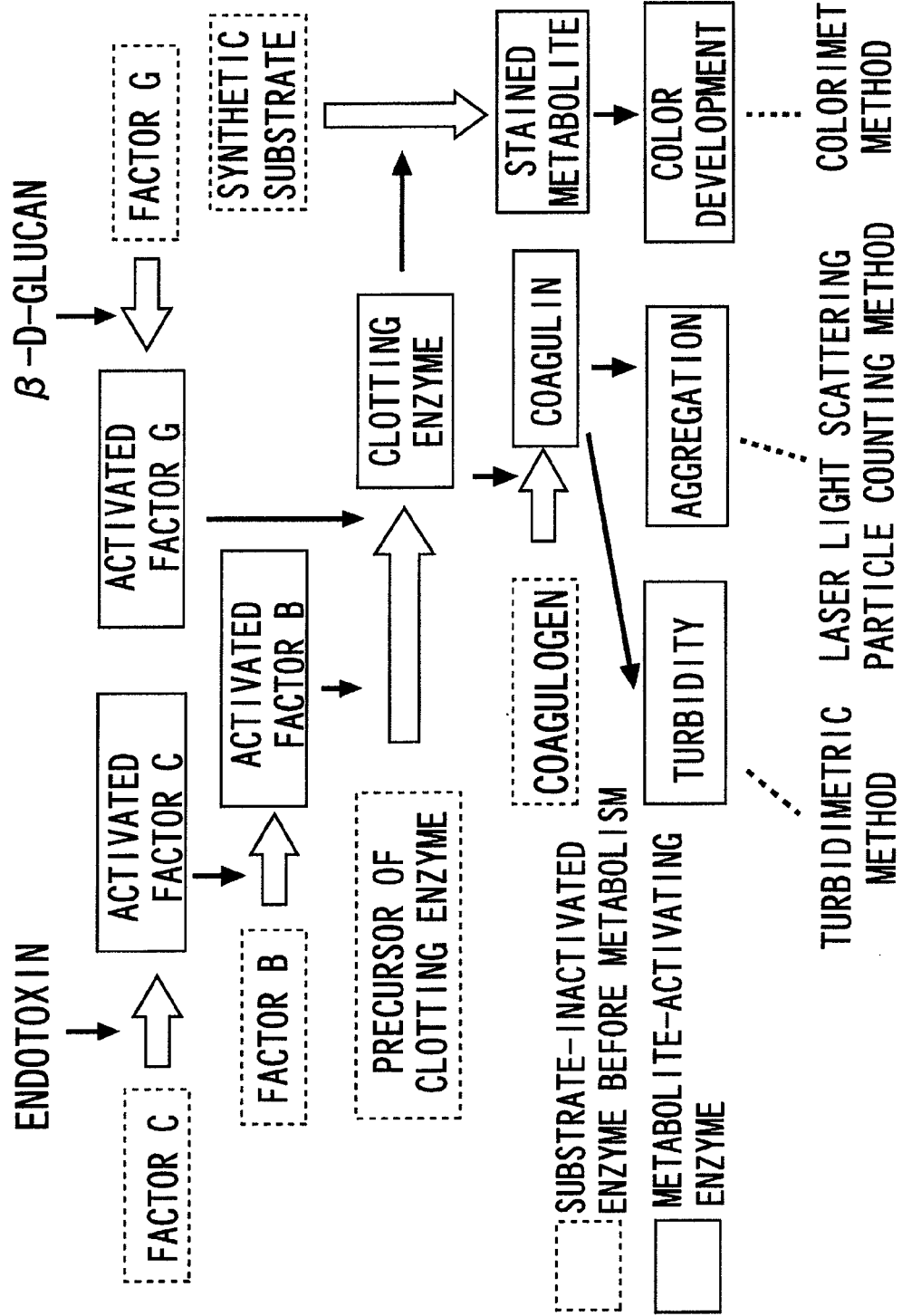
FIG. 6 is a schematic view to illustrate a process in which LAL is gelled by endotoxin or β-D-glucan and the detection method thereof.

The process of forming a gel by a reaction between LAL and endotoxin has been studied well. That is, as illustrated in FIG. 6, when endotoxin is bound to a serine protease, i.e., factor C in LAL, the factor C is activated to become activated factor C. The activated factor C hydrolyzes and activates another serine protease, i.e., factor B in LAL, and then the factor B is activated to become activated factor B. The activated factor B immediately hydrolyzes a precursor of clotting enzyme in LAL to form clotting enzyme, and further the clotting enzyme hydrolyzes a coagulogen in LAL to generate coagulin. Thus, the generated coagulin are then associated with each other to further form an insoluble gel, and the whole LAL is involved in the formation to turn into a gel.

In addition, similarly, when β-D-glucan is bound to factor G in LAL, the factor G is activated to become activated factor G. The activated factor G hydrolyzes a precursor of clotting enzyme in LAL to produce clotting enzyme. As a result, as is the case with the reaction between endotoxin and LAL, coagulin are generated, and the generated coagulin are associated with each other to further generate an insoluble gel.

The series of reactions as described above are similar to the process of forming a fibrin gel via serine proteases such as Christmas factor or thrombin present in mammals. Such enzyme cascade reactions have a very strong amplification effect because even a very small amount of an activation factor activates the subsequent cascade in a chain reaction. Therefore, according to a method of measuring a predetermined physiologically active substance using LAL, it is possible to detect a very small amount (sub-pg/mL order) of the predetermined physiologically active substance.

Examples of a measurement method which can quantify the predetermined physiologically active substance include the turbidimetric method and the laser light scattering particle counting method, as described above. In such measurement methods, measurement can be performed with a high sensitivity by detecting association products of coagulin formed by the enzyme cascade reactions in LAL as the turbidity of a sample in the former method or as fine gel-particles formed in the system in the latter method.

In particular, in the laser light scattering particle counting method, fine gel-particles formed in the system are directly measured, and hence the method is more sensitive than the turbidimetric method. In addition, gel formation can be detected in a short period of time compared with the turbidimetric method because in general, a sample containing LAL and an analyte is forcibly stirred.

In addition, another method of measuring endotoxin further includes a colorimetric method. As illustrated in FIG. 6, the method does not measure the turbidity of a sample caused by a coagulin gel although the method is based on the enzyme cascade reactions in LAL. The method utilizes such as synthetic substrate that is hydrolyzed by clotting enzyme to develop a color, and is performed by measuring absorbance changes caused by a reaction between an analyte and LAL containing the synthetic substrate. In the colorimetric method, the concentration of a chromogenic substance formed in the system is measured, and hence a lower concentration predetermined physiologically active substance can be measured in a shorter period of time compared with the turbidimetric method or laser light scattering particle counting method, in both of which gel formation in a sample is measured.

By the way, in the above-mentioned respective measurement methods, in the production process of an LAL reagent for measuring endotoxin or β-D-glucan, if endotoxin or β-D-glucan enters, gelation of a raw material occurs during production of the reagent depending upon the amount of the entered substances, which may make a resultant product unusable as a reagent. At that time, even when the entering amount of endotoxin or β-D-glucan is small, as mentioned above, the LAL reagent has an amplification effect by an enzyme cascade. Therefore, when it takes a long time to prepare a reagent, the entire reagent may be gelled.

For endotoxin, adsorbing substances such as polymyxin B and polylysine are known, and by applying such substances to the LAL reagent, the entered endotoxin can be removed. However, since already activated factor C, factor B, and clotting enzyme continue to act in the direction in which the coagulogen in the lowest downstream of enzyme cascade is hydrolyzed, with only the removal of endotoxin, the gelation of the LAL reagent cannot be prevented. The same is true to β-D-glucan.

The following is an example of the process for producing an LAL reagent or a coagulogen raw material using LAL as a material, which can suppress the gelation during production even if a minute amount of endotoxin or β-D-glucan enters. However, an LAL reagent and a process for producing a coagulogen raw material of the present invention are not limited to the following examples.

As the material of the coagulogen raw material according to the present invention, a limulus amoebocyte lysate, an LAL reagent produced by using the limulus amoebocyte lysate, as well as waste that cannot be used as a reagent because a minute amount of endotoxin or β-D-glucan enters therein, can be used. However, since an object of the present invention is to produce a coagulogen raw material having a function, materials in which most of the coagulogen is made into a coagulin and which are gelled are not included in the present invention. To such materials, if necessary, at least one or more of a substance that adsorbs endotoxin, a substance that adsorbs β-D-glucan, a substance that deactivates the action of endotoxin, and a substance that deactivates β-D-glucan may be added.

Examples of the substance that adsorbs endotoxin may include polymyxin B, polylysine, polyornithine, polyethylene imine, factor C itself and protein including a site of the factor C to which the endotoxin is bound, polypeptide and an antibody to which the endotoxin is bound. Examples of the substance that deactivates endotoxin may include an aqueous solution containing an iron ion, an aluminum ion, a chromium ion, a nickel ion, a cobalt ion, and a manganese ion, and a metal piece for supplying the ions.

Similarly, examples of the substance that is bound to β-D-glucan include lectin, a factor G itself and protein including a site of the factor G to which β-D-glucan is bound, polypeptide, and an antibody to which β-D-glucan is bound. Furthermore, in order to deactivate β-D-glucan, it is possible to consider that by reducing the hydrogen ion concentration of material, the solubility of β-D-glucan is reduced so as to be precipitated.

The material with which an optimal additive is mixed as necessary is then subjected to heat treatment. By carrying out the heat treatment at appropriate heating temperatures for an appropriate heating time, at least a part of a factor C, an activated factor C, a factor B, an activated factor B, a factor G, an activated factor G, precursor of clotting enzyme, and clotting enzyme, as a predetermined enzyme group in the material, is deactivated irreversibly. Thereby, the generation of the clotting enzyme due to the reaction with endotoxin or β-D-glucan is prevented. Thus, even if the material is contaminated with endotoxin or β-D-glucan, it is possible to obtain a coagulogen raw material that is not hydrolyzed into a coagulin and gelled.

Heating temperature and heating time of the heat treatment in this case may be adjusted appropriately depending upon the state of the material. For example, when the material is a solution, the reacting temperature is preferably 40° C. or more and 140° C. or less, and more preferably 60° C. or more and 100° C. or less. The preferable heating time is largely varied depending upon the heating temperatures, but it is preferably 30 seconds or more and 72 hours or less, and further preferably 10 minutes or more and 8 hours or less.

When the heating temperature is made too high, or the heating time is made too long, the LAL reagent or the protein in LAL becomes turbid due to denaturation, and cannot be used for a method of measuring turbidity of a sample, and coagulogen may be denatured and a function may be lost. Thus, cares need to be taken for heating temperature and heating time.

On the other hand, when the material is an LAL reagent that has already been in a form of a freeze-dried product, unlike the case where the material is a solution, higher heating temperature and longer heating time are required. The heating temperature is preferably 80° C. or more and 300° C. or less, and more preferably 100° C. or more and 250° C. or less. The preferable heating time varies depending upon the heating temperature as in the case where the material is an aqueous solution, but it is preferably 30 seconds or more and 72 hours or less, and more preferably 10 minutes or more and 8 hours or less.

In this way, pH of the heat-treated material is adjusted with various metal salts or ammonium salt, acid, alkali, and further, buffer solution and the like, if necessary, or surfactant or saccharides may be added if necessary.

The thus produced coagulogen raw material, as it is, is not subjected to gelation or aggregation reaction even when endotoxin or β-D-glucan is acted thereon. However, after the activated clotting enzyme is allowed to act thereon, or after an LAL reagent that has not been heat-treated is allowed to be mixed therewith, the coagulogen raw material is rapidly hydrolyzed into a coagulin and gelled or an aggregation reaction is induced, by endotoxin or β-D-glucan acting on the coagulogen raw material.

Furthermore, the coagulogen raw material produced by the present invention can be used for improvement of measurement sensitivity of endotoxin or β-D-glucan, shortening of the measurement time, improvement of measuring convenience, and the like. That is, when the coagulogen raw material of the present invention is mixed with an LAL reagent that has not been heat-treated, it is possible to prepare an LAL reagent whose coagulogen concentration is higher than usual. When endotoxin or β-D-glucan is allowed to act on the LAL reagent, more rapid measurement with high sensitivity can be carried out.

Furthermore, an LAL reagent in a state in which, for example, the coagulogen raw material of the present invention is bound or adsorbed to the surface of fine particles of polystyrene latex is prepared. Thereby, a method capable of significantly shortening time as compared with the measurement of endotoxin by a conventional turbidimetric method can be realized.

That is, when clotting enzyme activated by endotoxin or β-D-glucan is acted on an LAL reagent in which a coagulogen raw material is bound or adsorbed to the surface of polystyrene latex fine particles (hereinafter, also referred to as "beads"), the coagulogen is hydrolyzed into a coagulin by the enzyme cascade, and the formed coagulin allows fine particles to be associated with each other. Therefore, coagulogen in the coagulogen raw material obtained by the present invention is allowed to be bound or adsorbed to fine particles, whereby the fine particles can be associated with each other more efficiently, and an aggregated cluster can be formed earlier.

Methods for allowing coagulogen in the coagulogen raw materials of the present invention to be bound to beads may include a method of allowing the coagulogen to be adsorbed with electric charges of the beads, a method of using ionic property of the beads, a method of forming a functional group that can be reacted with protein in the coagulogen raw material on the surface of the beads, and chemically binding coagulogen to the beads by the use of a functional group and an amino group or a carboxyl group in protein, and the like, and any method may be employed.

By the way, when an operation of allowing the coagulogen to be bound or adsorbed to the beads by modifying materials of LAL is carried out, production takes a long time such as several hours. Therefore, it is affected by endotoxin or β-D-glucan entering in other materials in a minute amount, or a minute amount of a physiologically active substance may enter during an operation, and thus raw materials are gelled. An objective substance may not be obtained in this case.

To solve the problem, conventionally, measures of adding various enzyme inhibitors to the raw material have been considered. Examples of such enzyme inhibitors include diisopropylfluorophosphate, benzamidine, phenylmethanesulfonyl fluoride, 4-(2-aminoethyl)-benzenesulfonyl fluoride, 6-amidino-2-naphthyl-4-guanidinobenzoatedimethanesulfonate, p-amidinophenylmethylsulfonyl fluoride, aprotinin, antipain, leupeptin, ecotin, PPACK (Phe-Pro-Arg-chloromethylketone), α2-macroglobulin, and trypsin inhibitor.

However, when the coagulogen raw material of the present invention is used, only enzyme function in LAL is irreversibly deactivated while the coagulogen activity is maintained. Therefore, without adding the above-mentioned enzyme inhibitors, it is possible to prevent gelation of the raw material by endotoxin or β-D-glucan entering in the material during binding or adsorption to the beads.

Hereinafter, the detail of the process for producing a coagulogen raw material of the present invention is described. Production Example shows an example of the production process, and the production process according to the present invention is not limited to the conditions of the Production Examples mentioned below.

Production Example 1

A predetermined amount (0.15 mL) of distilled water for injection medicine (manufactured by Otsuka Pharmaceutical Co., Ltd.) was added to a freeze-dried product of an LAL reagent (Limulus ES-II Single Test Wako, manufactured by Wako Pure Chemical Industries, Ltd., hereinafter, abbreviated as "ES-II"), and they were mixed with each other in a vortex mixer. Thereafter, the mixture was placed in an Aluminum Block Heater (HDB-1N, manufactured by AS ONE Corporation. Unless particularly noted hereinafter, this type of machine is used for Aluminum Block Heater) that had been heated to a predetermined temperature (mentioned below) in advance and heated for a predetermined period of time (mentioned below). The mixture was cooled in ice immediately after heating to obtain an aqueous solution of a coagulogen raw material.

Production Example 2

A freeze-dried product of the LAL reagent (ES-II) as it was placed in the Aluminum Block Heater that had been heated to 120° C. in advance and heated for a predetermined period of time (mentioned below). The mixture was cooled in ice immediately after heating to obtain a freeze-dried product of a coagulogen raw material.

Production Example 3

Irreversible deactivation and maintaining of the coagulogen function of the enzymatic activity of the coagulogen raw materials obtained in Production Example 1 and Production Example 2 were evaluated by the laser light scattering particle counting method capable of quantifying endotoxin. In the laser light scattering particle counting method, a special-purpose glass container having $\phi$7 mm and length of 50 mm was used. The container is provided therein with a stainless steel stirring bar ($\phi$1 mm, length 5 mm) used for stirring a sample. In order to allow this container to be in an endotoxin-free state, an opening of the container was covered with an aluminum foil, and further 20 each of the container was packaged with aluminum foil and filled in a dried and heat-treated iron can, and it was heat-treated at 250° C. for three hours so as to thermally decompose endotoxin. The measurement container that had been made in an endotoxin-free state by dried heat treatment in this way was produced and used for tests.

Production Example 4

In order to examine the coagulogen function of the coagulogen raw material of the present invention, that is, to examine whether the coagulogen is hydrolyzed by an activated clotting enzyme to be gelled or the coagulogen exhibits an aggregation reaction, the activated product of clotting enzyme was obtained as follows. That is, 200 μL of aqueous solution of endotoxin having a concentration of 1.0 EU/mL was allowed to act on an LAL reagent (ES-II) that had not been heat-treated, and the mixture of the LAL reagent and the aqueous solution of endotoxin was transferred to the container manufactured in Production Example 3, and the stainless steel stirring bar inside the container was rotated by a stirrer disposed in the direction of the bottom surface of the container so as to allow the reaction to proceed while the temperature was kept at 37° C.

In the laser light scattering particle counting method, it is known that an LAL reagent that is gelled by endotoxin appears as a fine aggregated cluster by stirring, and the appearing time of the aggregated cluster and the concentration of endotoxin in the sample are plotted on the same line by log-log plot. In the case of this condition, the aggregation was detected for about six minutes, but stirring was continued also after the detection of aggregation, and the container was taken out from the apparatus at the time 20 minutes has passed from the starting of measurement. Then, a whole amount of gel aggregates inside the container was transferred to an endotoxin-free disposable centrifuging tube, centrifuged at 15000 rpm (radius of the rotor: 7 cm) for two minutes so as to precipitate a gel component containing a coagulin polymer as a main component. By another method, it was confirmed that centrifugation supernatant did not contain coagulogen. By this production process, the clotting enzyme activated by endotoxin was prepared.

Production Example 5

To an LAL reagent (ES-II), 0.2 mL of aqueous solution of endotoxin having a predetermined concentration (mentioned below) was added, and the mixture was mixed in a vortex mixer. Thereafter, the mixture was placed in an Aluminum Block Heater that had been heated to 100° C. and heated for 20 minutes. The mixture was cooled in ice immediately after heating to obtain an aqueous solution of the coagulogen raw material.

Production Example 6

A suspension (0.5 mL) of polystyrene latex fine particles (Polybeads Carboxylate Microspheres, 0.45 μm, solid part: 2.63%, manufactured by Polysciences Inc., hereinafter, abbreviated as "carboxyl beads") whose surface was carboxylated was centrifuged at 15000 rpm for 5 minutes in an endotoxin-free centrifuging tube (volume: 2.0 mL) with a screw cap, and the supernatant thereof was removed. Then, distilled water for injection was added so that the amount became 2.0 mL to be suspended, followed by centrifuging again to remove a supernatant. Removal of supernatant by the centrifugation was repeated again, followed by re-suspension in 1 mL of distilled water for injection, and then the suspension was transferred to an endotoxin-free centrifuging tube (volume: 15 mL) with a screw cap. Furthermore, 4 mL of distilled water for injection was added thereto and the mixture was placed to autoclave (121° C., 20 minutes), and thus endotoxin entering in the beads was deactivated and removed.

Carboxyl beads after autoclave were transferred to a centrifuging tube (volume: 2.0 mL) with a screw cap. Then, washing procedure including a set of the above-mentioned centrifugation, removal of the supernatant, and re-suspension in distilled water for injection was carried out twice in total. Next, to 10 mL of aqueous solution of water soluble carbodiimide (WSC, manufactured by DOJINDO LABORATORIES) dissolved in distilled water for injection, which was prepared so that the concentration was 20 mg/mL, 2 mL of 0.1M acetic acid buffer (pH4.98) was blended, and it was allowed to pass through the sterilization filter (manufactured by Milipore) having a hole diameter of $\phi$0.2 μm. To 0.5 mL of them, precipitate of the above-mentioned carboxyl beads was re-suspended.

Furthermore, to a freeze-dried product of LAL reagent (ES-II), 0.5 mL of distilled water for injection (manufactured by Otsuka Pharmaceutical Co., Ltd.) was added and dissolved, and subjected to heat-treatment at 60° C. for 10 minutes. The coagulogen raw material (0.5 mL) of the present invention obtained by the heat treatment, carboxyl beads suspension (0.5 mL) prepared by the above-mentioned method, and a TritonX-100 aqueous solution (10 μL) which is a nonionic surfactant that had been prepared so that the concentration was 1.0% (prepared with distilled water for injection, and then filtered through a sterilization filter having a hole diameter of φ0.2 μm) were mixed, and reacted at room temperature for two hours.

With this reaction, a carboxyl group of the carboxyl beads was activated by carbodiimide, then bound to an amino group of coagulogen by amide binding, and coagulogen is chemically bound to the surface of the beads. After the reaction, the reacted product was washed by carrying out a set of centrifugation, removal of the supernatant, and re-suspension of distilled water for injection as mentioned above twice in total. Then, 100 μL of 0.25 M aqueous solution of amino ethanol (prepared with distilled water for injection, and then filtered through the sterilization filter having a hole diameter of φ0.2 μm) was added, the mixture was stirred at room temperature for 20 minutes so as to deactivate the unreacted activated carboxyl group on the carboxyl beads. Thereafter, similarly, the product was washed with distilled water for injection three times in total, and re-suspended in 5 mL of distilled water for injection, and 50 μL each of the above-mentioned 1.0% aqueous solution of Triton X-100 and 2% aqueous solution of sodium azide (prepared with distilled water for injection, and then filtered through the sterilization filter having a hole diameter of φ0.2 μm) was added to obtain coagulogen-bound microbeads.

Hereinafter, Examples of the present invention are described.

Example 1

In Production Example 1, a coagulogen raw material was produced under the conditions in which the indicating temperature of the Aluminum Block Heater was any of 40° C., 50° C., 60° C., 70° C., 80° C., 100° C., and 120° C. and the heating time was 10 minutes, and 100 μL of the produced coagulogen raw material was placed in the measurement container manufactured in Production Example 3. To the container, 100 μL of 2.0 EU/mL aqueous solution of endotoxin was added and allowed to act, and measurement was carried out by the laser light scattering particle measurement apparatus (PA-200 manufactured by Kowa Company Ltd., hereinafter, abbreviated as "PA-200"). From the measured concentration (C=1.0 EU/mL) in the case where heat treatment had not been carried out and the measured concentration (S) in the heat-treated LAL reagent, the remaining clotting enzyme specific activity (A), which was enzymatic activity after heating, was defined and derived based on the following mathematical formula.

$$A = S/C \times 100 (\%) \quad (1)$$

Figure 1:
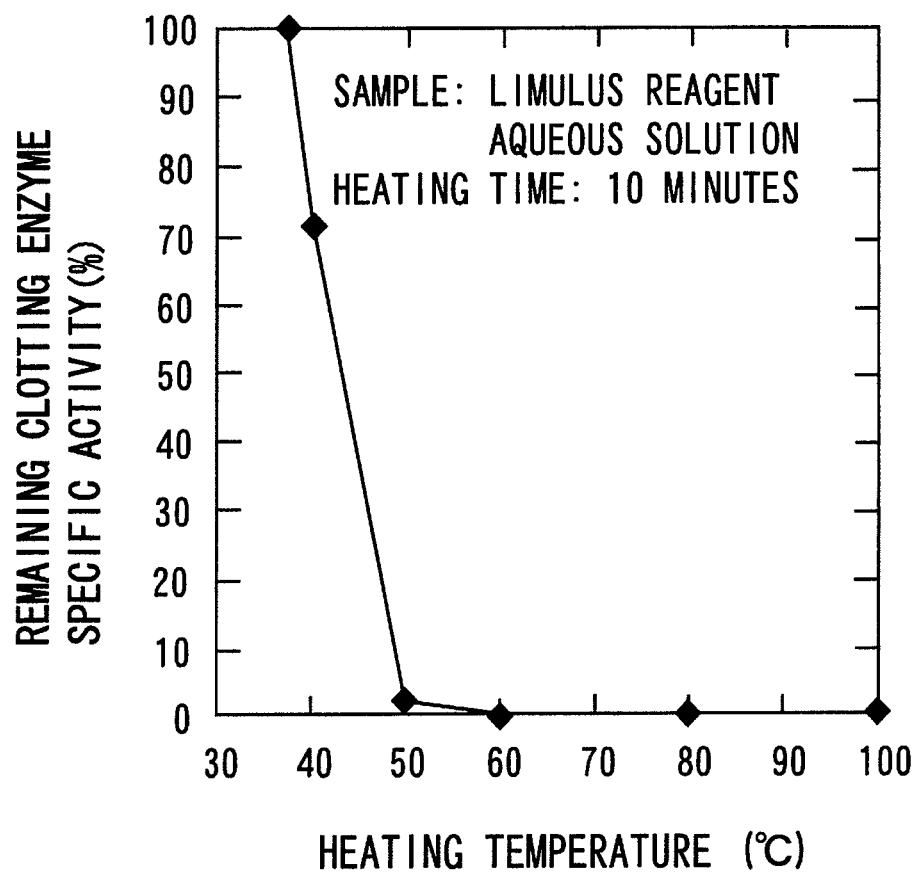
FIG. 1 is a graph showing a relation between a heating temperature of an aqueous solution of an LAL reagent and the remaining clotting enzyme specific activity in Example of the present invention.

FIG. 1 shows the relation between the resultant remaining clotting enzyme specific activity (A) and the heating temperature of the LAL reagent aqueous solution. As shown in FIG. 1, it has been revealed that in the case where the heating time is set at 10 minutes, the enzymatic activity is completely disappeared when the heating temperature becomes 60° C. or more. Furthermore, although not shown, as the heating temperature was higher, a phenomenon in which an aqueous solution of the coagulogen raw material after production was white turbid was observed. For example, when an aqueous solution of the coagulogen raw material was produced by heating at 120° C., most of the part was changed into white turbidity and insoluble substances, which were regarded to be caused by thermal denaturation. Therefore, it was shown that this heating condition was not suitable for actual use.

Example 2

In Production Example 1, the coagulogen raw material (150 μL) was produced under the conditions in which the indicating temperature of the Aluminum Block Heater was any of 40° C., 50° C., 60° C., 70° C., 80° C., 100° C., and 120° C., and the heating time was 10 minutes, and to the coagulogen raw material, 50 μL of aqueous solution of the activated clotting enzyme obtained in Production Example 4 was added and allowed to act, and the mixture was mixed in a vortex mixer for 5 seconds. The sample was transferred to the measurement container manufactured in Production Example 3, and aggregation starting time was measured by the laser light scattering particle measurement apparatus (PA-200).

Table 1 shows aggregation starting time with respect to each of the heating temperatures. At any heating temperature, aggregation starts in about 3 minutes after the aqueous solution of the activated clotting enzyme was added, showing that the function of the coagulogen was hardly affected by heating. Furthermore, in the treatment at such a high temperature as 120° C., most of protein in the LAL reagent was thermally denatured and coagulated, but the function of the remaining coagulogen itself was maintained, and aggregation started in about 4 minutes after the aqueous solution of activated clotting enzyme had been added. This shows that the coagulogen was extremely resistant to heating. Furthermore, as shown in Table 1, when the LAL reagent was subjected to heat treatment at a temperature of 80° C. or less so as to deactivate the enzymatic activity, white turbidity in the LAL reagent was hardly observed. Therefore, it is shown that by heat-treating the LAL reagent at 80° C. or less so as to deactivate the enzymatic activity, it is possible to obtain a coagulogen raw material which is suitable for optical measurement and which is highly usable.

TABLE 1

| Heating temperature (° C.) | Aggregation starting time (min) | State of aqueous solution |
|---|---|---|
| Not heat-treated | 2.33 | Transparent |
| 60 | 3.00 | Transparent |
| 80 | 2.33 | Slightly white turbid |
| 100 | 2.17 | White turbid |
| 120 | 4.00 | Many clotted substances were observed |

Example 3

In Production Example 2, the heating time was set to any of 10 minutes, 30 minutes, 60 minutes, 120 minutes, and 300 minutes, 1.0 EU/mL of aqueous solution of endotoxin (200 μL) was added to a freeze-dried product of the coagulogen raw material that had been heat-treated without opening the LAL reagent (Limulus ES-II Single Test Wako, manufactured by Wako Pure Chemical Industries, Ltd.). Then, the mixture was mixed in a vortex mixer for 5 seconds, and transferred to the measurement container manufactured in Production Example 3, where the activity of the enzyme remaining after heat treatment was determined by the laser light scattering particle measurement apparatus (PA-200). Then, the remaining clotting enzyme specific activity (%) defined by the above-mentioned formula (1) was calculated.

Figure 2:
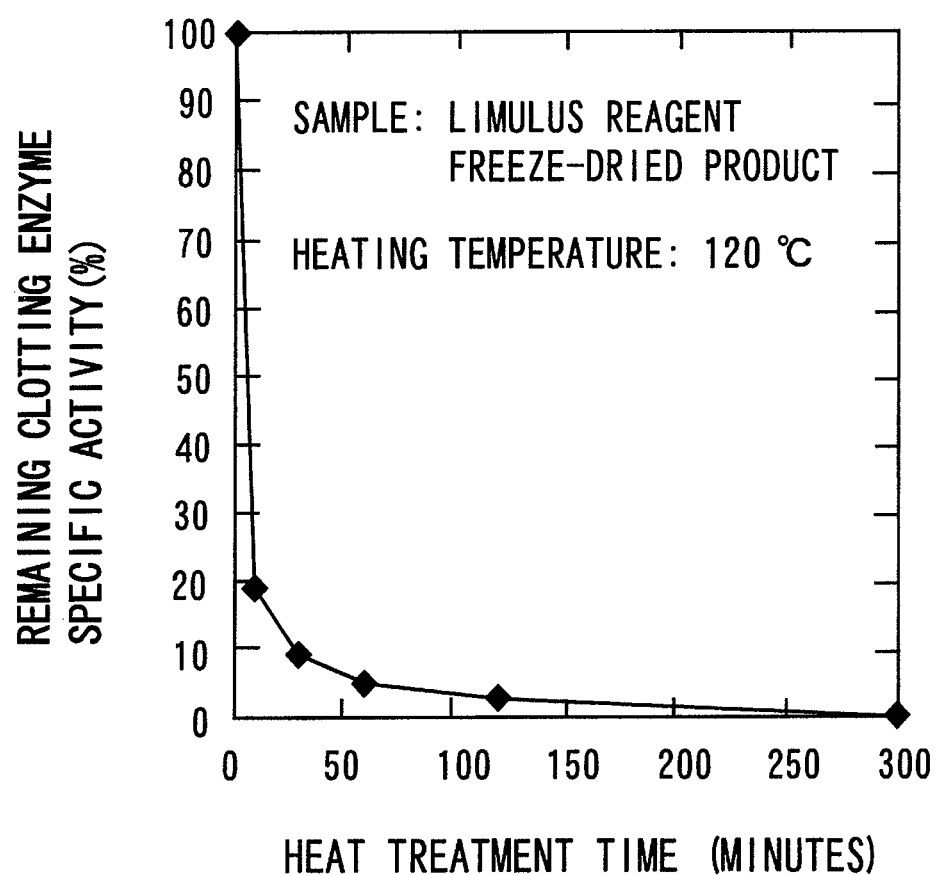
FIG. 2 is a graph showing a relation between a heating time of a freeze-dried product of an LAL reagent and the remaining clotting enzyme specific activity in Example of the present invention.

FIG. 2 shows a relation between a remaining clotting enzyme specific activity obtained in this Example and a heat treatment time of a freeze-dried product of an LAL reagent. As shown in FIG. 2, as compared with the case of Example 1, it is shown that even if heat treatment is carried out at a high temperature for a longtime, the enzymatic activity does not completely disappear. However, by heat treatment at 120° C.

for 300 minutes, the remaining clotting enzyme specific activity was reduced to about 0.2%. In the thus produced coagulogen raw material, the color of the aqueous solution obtained by dissolving the raw material in water tended to turn a little bit yellow, but white turbidity or generation of coagulated insoluble substances did not occur, and the coagulogen raw material was rapidly dissolved in water.

Example 4

Example 4 examined a relation between the concentration of endotoxin that has entered and the degree of deactivation of enzyme by heat treatment when the LAL reagent is subjected to heat treatment in a state in which endotoxin has entered in advance. The endotoxin concentration of the aqueous solution of endotoxin that had entered in Production Example 5 was made to be 10, 1, and 0.1 EU/mL, and coagulogen raw materials containing endotoxin having respective concentrations were obtained.

Next, in this Example, in order to compare with the above-mentioned coagulogen raw material into which endotoxin had entered, a control coagulogen raw material was prepared by heating an LAL reagent dissolved in 0.2 mL of distilled water for injection (manufactured by Otsuka Pharmaceutical Co., Ltd.) not containing endotoxin according to the procedure shown in Production Example 5. Furthermore, dilution series of aqueous solutions of endotoxin was formed, and 200 μL of each was placed in an LAL reagent (ES-II) that had not been heat-treated and the mixture was stirred in a vortex mixer for 5 seconds, after which 100 μL each of the sample was taken, and then mixed with 100 μL of the above-mentioned control coagulogen raw material, and calibration curve of the concentration of endotoxin was obtained by the laser light scattering particle measurement apparatus (PA-200).

Next, the LAL reagent (ES-II) that had not been heat-treated was dissolved in 200 μL of distilled water for injection (manufactured by Otsuka Pharmaceutical Co., Ltd.), and 100 μL of them was mixed in a vortex mixer for 5 seconds with 100 μL of the above-mentioned respective coagulogen raw materials in which endotoxin had entered. Then, the concentration of endotoxin was calculated in the comparison with the above-obtained calibration curve with the use of the laser light scattering particle measurement apparatus (PA-200). The obtained results are shown in Table 2. As shown in Table 2, in any samples, the measured concentration of endotoxin was lower than the concentration of endotoxin that had actually entered. Then, as shown in the activity remaining rate after heating in Table 2, the reduction degree from the actual value of the resultant concentration of endotoxin was larger as the concentration of the endotoxin to be entered was lower. Thus, it has been revealed that as the concentration of the endotoxin that has previously entered is lower, the effect of the deactivation of enzyme by heat treatment is large.

TABLE 2

| Concentration of entering endotoxin (EU/mL) | Measured concentration after heating(EU/mL) | Activity remaining rate after heating(%) |
|---|---|---|
| 10.00 | 3.11 | 31.1 |
| 1.00 | 0.18 | 17.6 |
| 0.100 | 0.004 | 4.4 |

Example 5

By using the coagulogen-bound microbeads produced in Production Example 6, the concentration of endotoxin in the dilution series of the aqueous solution of endotoxin was measured by using a stirring turbidimetric method (hereinafter, this measurement method is defined as "coagulogen-bound microbeads method".). The stirring turbidimetric method is different from a conventional turbidimetric method in that the concentration of endotoxin is measured while stirring a sample and measuring the degree of change of the transmittance of the sample.

Figure 3:
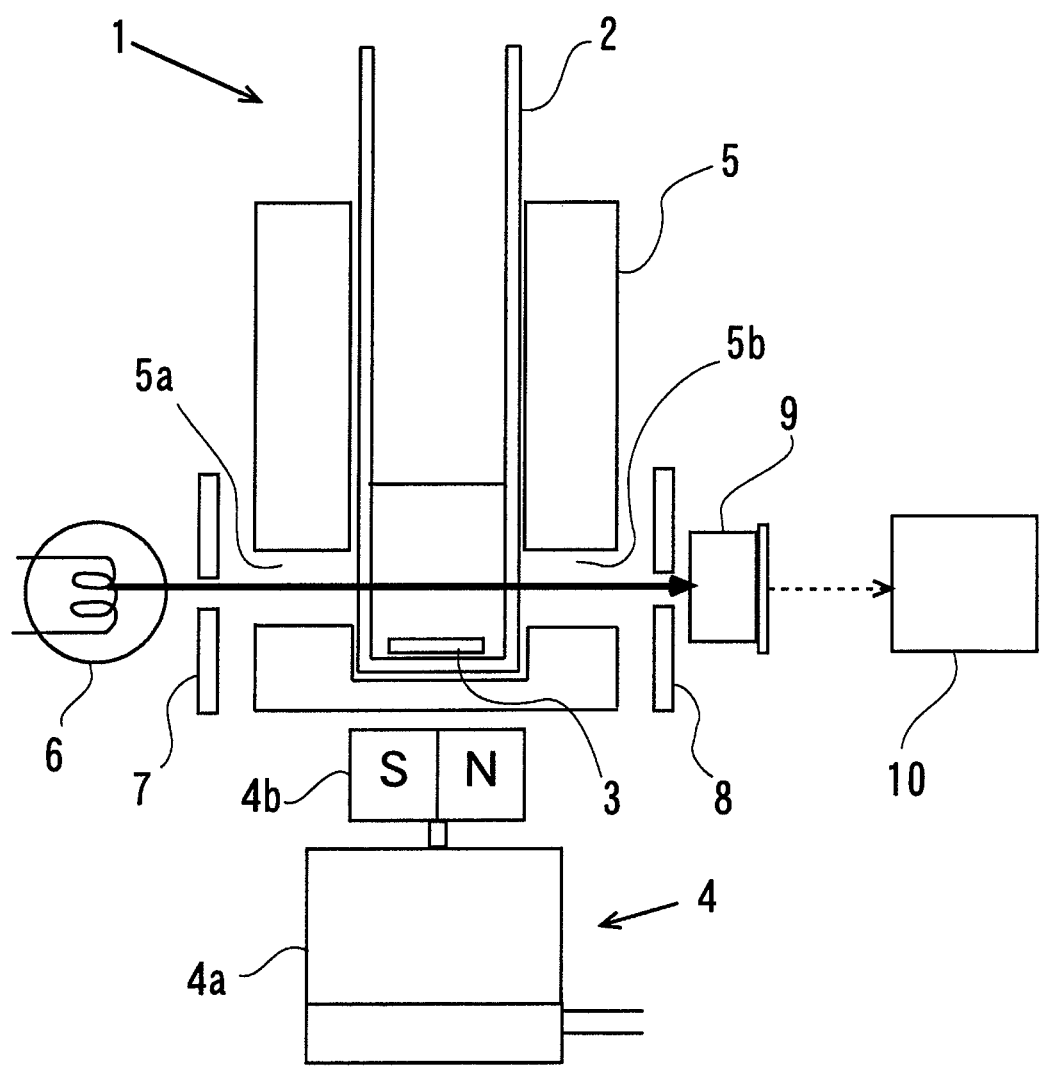
FIG. 3 is a view showing a schematic configuration of a turbidimetric measurement apparatus in Example of the present invention.

FIG. 3 shows a schematic configuration of a turbidimetric measurement apparatus 1 as a stirring turbidimetric measurement apparatus of this Example. In the stirring turbidimetric method of this Example, a sample is transferred to a special-purpose glass vessel 2 as a liquid mixture retaining portion. A warmer 5 is provided so as to surround the glass vessel 2. The inside of this warmer 5 is provided with heating wire (not shown). By allowing this heating wire to carry electricity, the glass vessel 2 is kept warm at about 37° C. This glass vessel 2 is provided with a stirring bar 3 made of stainless steel. The stirring bar 3 is rotated in the glass vessel 2 by the action of a stirrer 4 provided in the lower part of the glass vessel 2. That is, the stirrer 4 includes a motor 4a and a permanent magnet 4b provided on an output shaft of the motor 4a. Then, by allowing the motor 4a to carry electricity, the permanent magnet 4b is rotated. A magnetic field from the permanent magnet 4b is rotated, and thereby the stirring bar 3 made of stainless steel is rotated by the action of the rotating magnetic field. The stirring bar 3 and the stirrer 4 correspond to a stirring portion.

Note that the turbidimetric measurement apparatus 1 includes a light source 6 as a light incidence portion and a light receiving element 9 as a light receiving portion. Light emitted from the light source 6 passes through an aperture 7, then passes through a light incident hole 5a provided in the warmer 5, and is incident on a sample in the glass vessel 2. The light that transmits through the sample in the glass vessel 2 is emitted from an emission hole 5b provided in the warmer 5, passes through an aperture 8, and then the light receiving element 9 is irradiated with the light. The light receiving element 9 outputs a photoelectric signal corresponding to the intensity of the received light. With the output of the photoelectric signal, the transmittance of the sample is calculated in an arithmetic unit 10 as a deriving portion.

Two of LAL reagents (ES-II) that had not been heat-treated were dissolved in 200 μL of distilled water for injection, to which 50 μL of coagulogen-bound microbeads produced in Production Example 6 was placed, and the mixture was stirred in a vortex mixer for 5 seconds to obtain a coagulogen-bound microbeads/LAL reagent mixture. 50 μL of any of the dilution series of the aqueous solution of endotoxin with any of 2, 0.2, 0.02, and 0.002 EU/mL and 50 μL of the above-mentioned coagulogen-bound microbeads/LAL reagent mixture were placed in the glass vessel 2 produced according to the above-mentioned Production Example 3, and measured by the turbidimetric measurement apparatus 1.

In the coagulogen-bound microbeads, when clotting enzyme in the LAL reagent is activated by acted endotoxin, similarly, coagulogen contained in the LAL reagent is made into a coagulin and at the same time, coagulogen on the coagulogen-bound microbeads is also hydrolyzed into a coagulin, but beads are cross-linked by these coagulins to make a large aggregated cluster. The sample originally contains a large amount of simple substances of beads and is highly turbid. However, since the beads concentration of the simple substance is rapidly reduced by aggregation, the light transmittance of the sample is increased. In the coagulogen-bound microbeads method, the time at which aggregated clusters start to be generated is determined with such a rapid increase in the light transmittance.

Figure 4A:
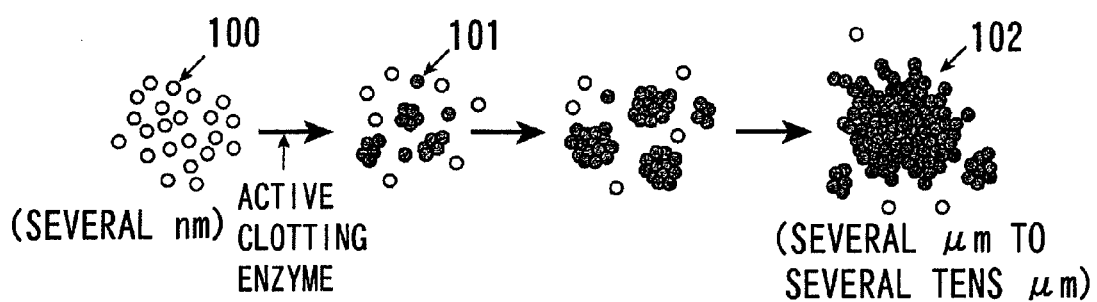
FIG. 4A illustrates a gelation-aggregation process of coagulogen by an active clotting enzyme.
Figure 4B:
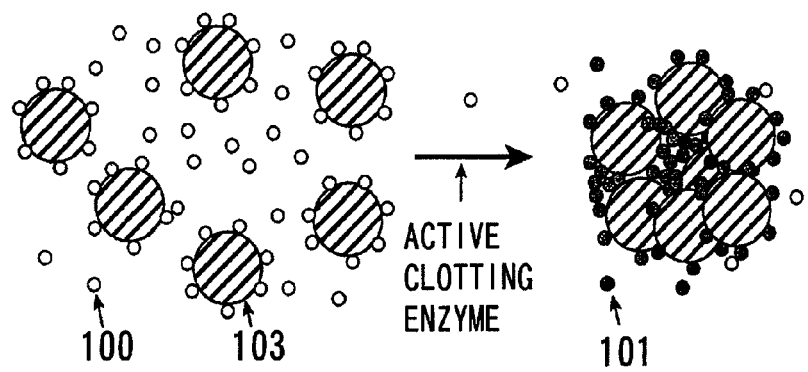
FIG. 4B illustrates a process of aggregation of coagulogen-bound microbeads.

FIG. 4A shows conventional gelation and aggregation process of coagulogen by an active clotting enzyme, and FIG. 4B shows gelation and aggregation process of coagulogen by a coagulogen-bound microbeads method. FIG. 4A shows conventional gelation and aggregation process of coagulogen by an active clotting enzyme. As shown in FIG. 4A, coagulogen 100 having a particle diameter of about several nm is hydrolyzed into coagulins 101 by an active clotting enzyme. These coagulins 101 are aggregated into a multimer and form gel particles in the stirring turbidimetric method. Thereafter, with the passage of time, the aggregation of the coagulins 101 further proceeds and the particle diameter of the gel particle is gradually increased. Then, when a relatively long lag time has passed, measurable gel particles 102 having a particle diameter of several μm to several tens μm are obtained.

On the contrary, in the coagulogen-bound microbeads method, as shown in FIG. 4B, when an active clotting enzyme acts on the coagulogen 100 bound to a bead 103, the coagulogen 100 on the bead 103 is hydrolyzed by enzyme cascade into the coagulins 101. In the process in which the coagulins 101 are aggregated, the coagulins 101 associate the beads 103 to each other. Thus, the diameter of the particles including the coagulin 101 and the bead 103 as main components rapidly increases, making it possible to obtain a measurable particle diameter in a short lag time. Note that it has been clear that this aggregation reaction is extremely stronger than the aggregation reaction induced by the LAL simple substance.

Figure 5:
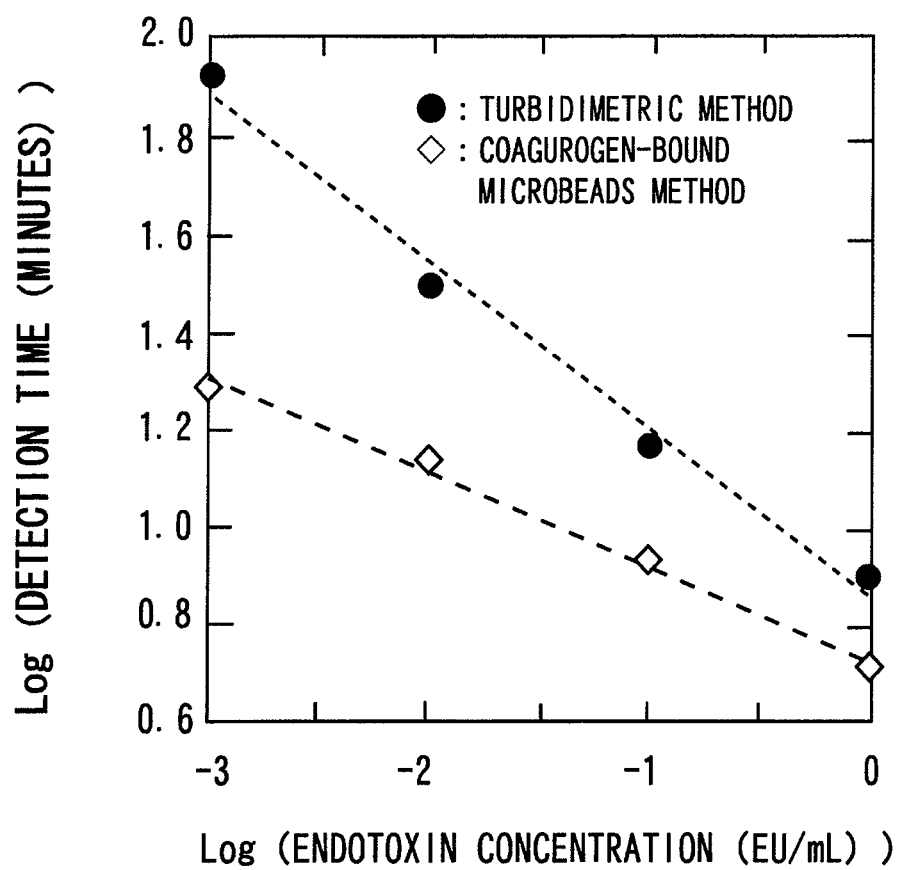
FIG. 5 is a graph showing a comparison of an endotoxin dose reaction between a coagulogen-bound microbeads method and a turbidimetric method.

Furthermore, in this Example, in order to compare with a case using the coagulogen-bound microbeads method, the concentration of endotoxin was measured also by the turbidimetric method. In the turbidimetric method, to an LAL reagent that had not been heat-treated, 100 μL of injectable solution, and 100 μL of samples having any concentrations of the aqueous solution of endotoxin dilution series were placed and measurement was carried out by using a turbidimetric device (Toxinometer ET-2000, manufactured by Wako Pure Chemical Industries, Ltd.). Results of comparison between the coagulogen-bound microbeads method and the turbidimetric method are shown in FIG. 5. In both measurement methods, when the axis of abscissa shows the concentration of endotoxin and the axis of ordinate shows detection time, the logarithmic plot of the both axes was approximated to line. The approximating curve was Y=−0.190X+0.738 for the coagulogen-bound microbeads method, and Y=−0.349X+0.869 for the turbidimetric method, showing that measurement time can be significantly reduced in the coagulogen-bound microbeads method as compared with the turbidimetric method, and that as the concentration of the endotoxin to be acted is lower, the difference in time period necessary for measurement is larger. Actual time periods necessary for measurement, and the like, are summarized in Table 3.

TABLE 3

| Endotoxin acting concentration (EU/mL) | Measurement period of time (minutes) | | Ratio of detection time (beads method/ Turbidimetric method) |
| --- | --- | --- | --- |
| | Microbeads method | Turbidimetric method | |
| 1 | 5.25 | 8.05 | 0.65 |
| 0.1 | 8.71 | 14.95 | 0.58 |
| 0.01 | 13.96 | 31.85 | 0.44 |
| 0.001 | 19.29 | 84.65 | 0.23 |

In this Example, materials of the beads 103 are not particularly limited, but examples of the materials include, in addition to polystyrene latex resin, silica, silicon resin, cellulose resin, polyvinyl alcohol resin, and hydroxyapatite, and polystyrene latex resin, silica, and cellulose resin are desirable.

Furthermore, the beads 103 having the size in the range of 0.05 μm to 50 μm are used in view of conditions capable of optically detecting the aggregation in an early stage, easiness in handling at the time of preparation, easiness of dispersing into a system and the like. In order to allow the coagulogen to be bound to the surface of the beads 103, a method of adsorbing the coagulogen electrostatically, hydrophilically, or hydrophobically, and a method of chemically binding the coagulogen are considered.

REFERENCE SIGNS LIST 1 turbidimetric measurement apparatus
2 glass vessel
3 stirring bar
4 stirrer
4a motor
4b magnet
5 warmer
5a light incident hole
5b emission hole
6 light source
7 aperture
8 aperture
9 light receiving element
10 arithmetic unit
100 coagulogen
101 coagulin
102 aggregation particle
103 bead

What is claimed is:

1. A process for producing a coagulogen raw material used for detecting a predetermined physiologically active substance of biological origin or measuring a concentration of the physiologically active substance, comprising:
heat-treating limulus amoebocyte lysate (LAL) at a temperature between 60° C. and 80° C. for a period of 10 minutes to 8 hours to produce the coagulogen raw material, wherein the LAL is supplied as a solution and comprises at least one enzyme selected from the group consisting of factor C, factor B, factor G, and precursor of clotting enzyme, and wherein said heat-treating inactivates at least a part of the enzyme in the LAL while maintaining activity of the coagulogen;
whereby when an enzyme cascade is generated by the physiologically active substance activating the enzyme, the coagulogen in the coagulogen raw material is hydrolyzed into coagulin by the enzyme cascade.

2. A process for producing a coagulogen raw material used for detecting a predetermined physiologically active substance of biological origin or measuring a concentration of the physiologically active substance, comprising:
heat-treating limulus amoebocyte lysate (LAL) at a temperature between 100° C. and 250° C. for a period of 300 minutes or more to produce the coagulogen raw material, wherein the LAL is supplied as a freeze-dried product and comprises at least one enzyme selected from the group consisting of factor C, factor B, factor G, and precursor of clotting enzyme, and wherein said heat-treating inactivates at least a part of the enzyme in the LAL while maintaining activity of the coagulogen;

whereby the coagulogen in the coagulogen raw material is hydrolyzed into coagulin by an enzyme cascade generated when the enzyme is activated by the physiologically active substance.

* * * * *